United States Patent [19]

Bringhurst et al.

[11] Plant 4,489

[45] Nov. 20, 1979

[54] STRAWBERRY PLANT

[75] Inventors: Royce S. Bringhurst, Davis; Victor Voth, Santa Ana, both of Calif.

[73] Assignee: The Regents of the University of California, Berkeley, Calif.

[21] Appl. No.: 953,993

[22] Filed: Oct. 23, 1978

[51] Int. Cl.[2] ..... A01H 5/03

[52] U.S. Cl. ..... Plt./49

[58] Field of Search ..... Plt./49, 48

*Primary Examiner*—Robert E. Bagwill

*Attorney, Agent, or Firm*—Townsend and Townsend

[57] ABSTRACT

A new and distinct variety of strawberry plant of a day-neutral type characterized by its ability after summer planting in South Coastal California to produce fruit during November, December and January, when California fruit is unavailable from the standard short-day cultivars and its ability after winter and spring plantings in Central Coastal California to produce spring and summer fruit without plant storage. Bract leaves do not normally occur on the petioles in contrast to the important California short-day cultivars. The plants are vigorous and prolific runner makers and with a minimum of conditioning, the new cultivar will flower and fruit effectively independent of day length. The fruit is long conic to flat wedged and fruit color is frequently uneven or burnished, though glossy. Flavor quality is almost equal to the important California short-day cultivars and shipping quality is adequate.

2 Drawing Figures

1

This invention relates to a new and distinctive day-neutral type strawberry cultivar designated as "CN8" which is the result of a cross between "Tufts" (U.S. Plant Pat. No. 3,561) and Cal 65.65-601 (not patented), a second generation backcross derivative from *Fragaria virginiana glauca* from Utah.

CN8 first fruited at the Wolfskill Experimental Orchards of the University of California near Davis in 1971 where it was selected in 1972 and designated originally as Cal 70.3-108.

CN8 has since been tested with varying results and asexually reproduced by runners at various University of California Field Stations and facilities and has also been favorably tested in a limited way, in representative growers' fields under strict control. Meristem originated virus negative stock for propagation has been developed by the University of California.

FIG. 1 of the accompanying photographic color reproduction shows typical growth, flowering and fruiting characteristics.

Figure 1:
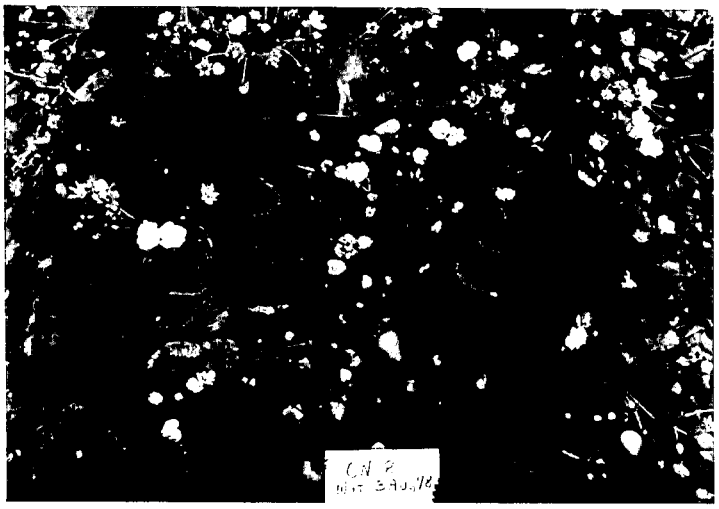
Figure 2:
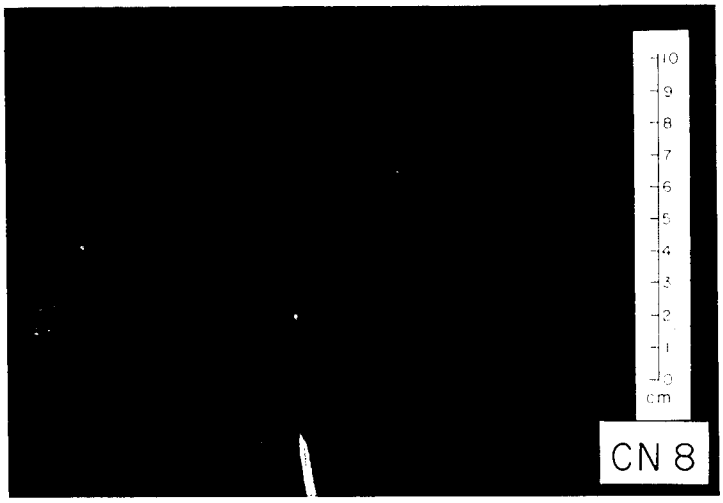
FIG. 2 shows a typical mid-summer mature leaf from a spring planted plant.
Figure 3:
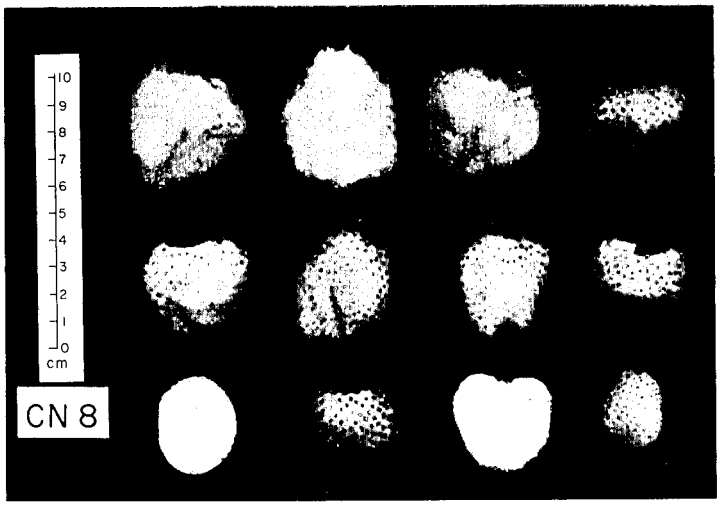
FIG. 3 shows representative mid-season fruit of CN8 with longitudinal and cross section views.

CN8 has performed well in winter fruiting experiments with summer planted plants in south coastal California and in spring to summer fruiting experiments in winter and spring plantings in central Coastal California. In Southern California CN8 can be programmed to produce fruit approximately 3 months after planting during November, December and January, months during which California fruit is not available from the standard short-day cultivars such as "Tioga" (not patented) and "Tufts" (U.S. Plant Pat. No. 3,561). Using the same 3 month rule, CN8 can be programmed to produce spring and summer fruit, beginning approximately 3 months after planting with or without plant storage and continuing on a cyclic basis throughout the summer and fall.

The distinctive characteristics of this new strawberry cultivar described below were observed upon its discovery and/or through the test period.

2

DESCRIPTION

Plants and foliage: CN8 plants are erect in growth habit very similar to "Tufts"; medium large in plant size similar to "Tufts". Bract leaves do not occur normally on the petioles of CN8 in contrast to the important California short-day cultivars. Leaflets of CN8 are about the same size as those of "Tufts" and are lighter and more yellow in color than those of "Tufts" about 10 Y 5/5 vs. 7.5 GY 5/7, respectively (Munsell Color System — Nickerson Color Fan). The leaflets of CN8 have about the same number of serrations as those of "Tioga" and "Aiko" (av of ±10/half blade), fewer than "Tufts" (±12) as averaged over the half blades of the 3 leaflets on mid-season mature leaves at Watsonville. CN8 plants are vigorous and prolific runner makers in the nursery. Runner production in the fruiting beds also occurs at varying rates and the runner plants always flower within a reasonable period of time whether rooted or not. CN8 differs from other so called "everbearing" types in that CN8 has a very low chilling requirement and consequently will fruit in the winter under adequate temperature conditions.

Isozymes in leaf extracts—Phosphoglucose isomerase (PGI): CN8 gave a five banded pattern similar to that of "Aiko" 30/35 35/35 35/35 35/40 mm, distinctive from the "Tioga" single band and "Tufts" slow three banded pattern (Scandalios. 1969. Biochem. Genet. 3:37–79).

Flowering and flowers: CN8 is a new type of cultivar in that with a minimum of conditioning it will flower and fruit anytime, effectively independent of day length. The inflorescences are very long and similar to those of "Tufts". The flowers are highly self fertile with ample pollen throughout the season.

Fruit and fruiting: CN8 has long conic to flat wedged fruit sometimes hollow centered often with a small neck, very similar in shape to that of "Tufts". The fruit skin color is about the same as that of "Tufts", about 7.5 R 4/11 (ibid) but color is frequently uneven or burnished in appearance and although it is very glossy the unevenness sometimes detracts seriously. The flesh color is similar to that of the skin and the core is light.

The achenes are frequently exserted similar to or more so than those of "Tufts". The calyx is small and usually reflexed. CN8 fruit is about as firm and durable as that of "Tufts" giving penetrometer readings of about ±6.6. The average fruit size is almost as large as that of "Tufts" (within 2 grams), larger than "Tioga" or "Aiko".

Fruit quality—Ascorbic acid: CN8 has averaged ±46 mg/100 g of fresh fruit, greater than that of "Tioga" (±40), about the same as "Tufts" (±45) and much less than "Aiko" (±60) as tested by the method of Loeffler and Ponting. 1942 J. Ind. and Eng. Chem. 14:846. Soluble solids: CN8 averaged ±7.2 but this was not significantly different from that of "Aiko", "Tioga" or "Tufts" according to our test of mid-summer Watsonville fruit. The flavor of CN8 is almost equal to that of the important California short-day cultivars in our opinion. CN8 is adequate for shipping if good quality control on color is maintained. It should be tested for home garden use where it might be of interest.

We claim:

1. The new and distinct variety of strawberry plant herein described and illustrated, and identified by the characteristics enumerated above.

* * * * *